United States Patent
Li et al.

(10) Patent No.: US 9,940,469 B2
(45) Date of Patent: Apr. 10, 2018

(54) ENCRYPTED DATA STORE FOR RECORDS

(75) Inventors: Jun Li, Mountain View, CA (US); Ram Swaminathan, Cupertino, CA (US); Sharad Singhal, Belmont, CA (US)

(73) Assignee: EntIT Software LLC, Sunnyvale, CA (US)

( * ) Notice: Subject to any disclaimer, the term of this patent is extended or adjusted under 35 U.S.C. 154(b) by 0 days.

(21) Appl. No.: 14/421,759

(22) PCT Filed: Aug. 30, 2012

(86) PCT No.: PCT/US2012/053215
§ 371 (c)(1),
(2), (4) Date: Feb. 13, 2015

(87) PCT Pub. No.: WO2014/028035
PCT Pub. Date: Feb. 20, 2014

(65) Prior Publication Data
US 2015/0220746 A1    Aug. 6, 2015

(51) Int. Cl.
| | |
|---|---|
| G06F 11/30 | (2006.01) |
| G06F 21/60 | (2013.01) |
| G06Q 50/24 | (2012.01) |
| G06Q 10/10 | (2012.01) |
| G06F 19/00 | (2018.01) |
| G06F 12/14 | (2006.01) |

(52) U.S. Cl.
CPC .......... *G06F 21/602* (2013.01); *G06F 19/322* (2013.01); *G06Q 10/10* (2013.01); *G06Q 50/24* (2013.01)

(58) Field of Classification Search
CPC ................. G06F 21/602; G06F 19/322; G06F 17/30342; G06Q 10/10; G06Q 50/24

USPC .................. 380/28–30, 44–47, 255–286; 713/150–154, 160–167, 189–193
See application file for complete search history.

(56) References Cited

U.S. PATENT DOCUMENTS

| | | | |
|---|---|---|---|
| 2003/0033169 A1 * | 2/2003 | Dew | .............. G06F 19/322 |
| | | | 705/3 |
| 2003/0074564 A1 | 4/2003 | Peterson | |
| (Continued) | | | |

FOREIGN PATENT DOCUMENTS

| | | |
|---|---|---|
| CN | 102331998 | 1/2012 |
| CN | 102457508 | 5/2012 |
| (Continued) | | |

OTHER PUBLICATIONS

International Search Report and Written Opinion of the International Searching Authority, dated Feb. 27, 2013; issued in related PCT Application No. PCT/US2012/053215.

(Continued)

*Primary Examiner* — Evans Desrosiers

(57) ABSTRACT

A method performed by a processing system includes determining a location in a metadata tree of a patient for an electronic health record, generating a record key for the electronic health record based on the location and a provider key corresponding to a provider, the provider key generated from a patient key corresponding to the patient, encrypting the electronic health record using the record key to generate a encrypted record, and providing the encrypted record to an encrypted data store.

15 Claims, 7 Drawing Sheets

(56) References Cited

U.S. PATENT DOCUMENTS

| | | | |
|---|---|---|---|
| 2003/0200213 | A1 | 10/2003 | Charlot et al. |
| 2005/0256742 | A1 | 11/2005 | Kohan et al. |
| 2008/0172737 | A1 | 7/2008 | Shen et al. |
| 2009/0112882 | A1* | 4/2009 | Maresh ................ G06F 19/321 |
| 2009/0150289 | A1 | 6/2009 | Joe et al. |
| 2009/0150292 | A1 | 6/2009 | Trinh et al. |
| 2009/0193267 | A1 | 7/2009 | Chung |
| 2010/0030690 | A1 | 2/2010 | Herlitz |
| 2013/0006865 | A1* | 1/2013 | Spates .................... G06Q 50/24 705/50 |

FOREIGN PATENT DOCUMENTS

| | | |
|---|---|---|
| JP | H09-114741 | 5/1997 |
| JP | 2005-115565 | 4/2005 |
| JP | 2005-539423 | 12/2005 |
| JP | 2006-099548 | 4/2006 |
| JP | 2008-237426 | 10/2008 |
| KR | 10-2002-0026284 A | 4/2002 |

OTHER PUBLICATIONS

Li, Z-R et al, "A Secure Electronic Medical Record Sharing Mechanism int he Cloud Computing Platform", Jun. 14-17, 2011.

Zhang, R et al, "Security Models and Requirements for Healthcare Application Clouds", Jul. 5-10, 2010.

Extended European Search Report dated Mar. 6, 2017 for EP Application No. 12891380.3; pp. 12.

Josh Benaloh et al: "Patient Controlled Encryption: Ensuring Privacy of Electronical Medical Records", CCSW '09: Proceedings of the 2009 ACM Workshop on Cloud Computing Security, ACM, US, Nov. 13, 2009 (Nov. 13, 2009), pp. 103-114, XP058150172.

Shivaramakrishnan Narayan et al: "Privacy preserving EHR system using attribute-based infrastructure", Proceedings of the 2010 ACM Workshop on Cloud Computing Secruity Workshop, CCSW, '10, ACM Press, New York, New York, USA, Oct. 8, 2010 (Oct. 8, 2010), pp. 47-52, XP058182232.

\* cited by examiner

ENCRYPTED DATA STORE FOR RECORDS

CROSS REFERENCE TO RELATED APPLICATION

This application claims priority to U.S. Provisional Patent Application No. 61/683,694, entitled "Secure Storing and Sharing of Electronic Medical Records in the Cloud Environment", and filed Aug. 15, 2012. The disclosure of this application is incorporated by reference herein.

BACKGROUND

Electronic Health Records (EHRs) may enable healthcare participants (e.g., patients, healthcare providers, payers, and researchers) to improve coordination of care and access to health information. Although EHRs may facilitate access to healthcare information, the sharing of healthcare information may involve many complex technical and legal issues. These issues may be burdensome for healthcare participants that lack the resources and expertise to enable such sharing while ensuring consistency, privacy, and security of the healthcare information.

DETAILED DESCRIPTION

Figure 1:
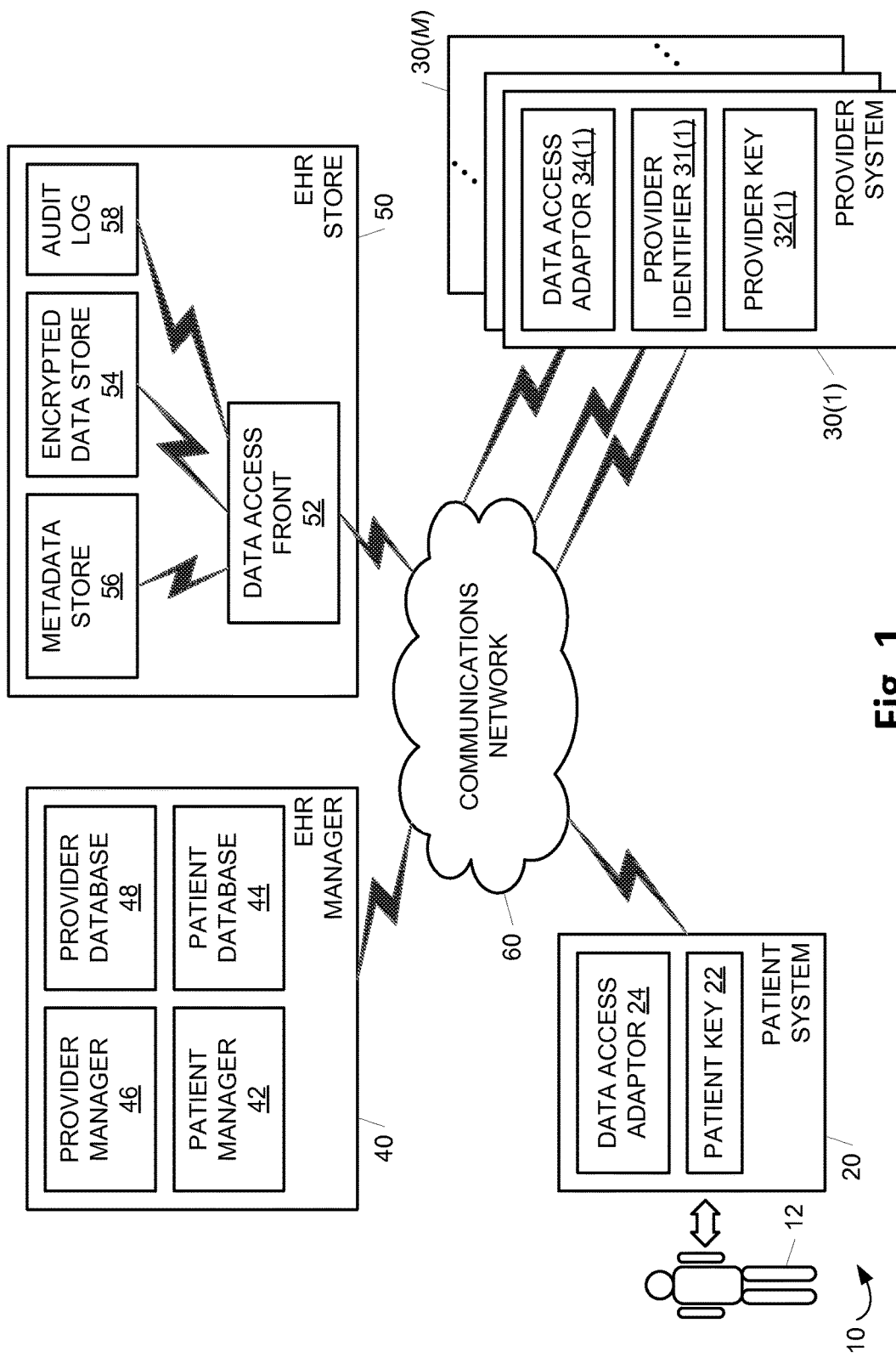
FIG. 1 is a block diagram illustrating one embodiment of an electronic health record store processing environment.

In the following detailed description, reference is made to the accompanying drawings, which form a part hereof, and in which is shown by way of illustration specific embodiments in which the disclosed subject matter may be practiced. It is to be understood that other embodiments may be utilized and structural or logical changes may be made without departing from the scope of the present disclosure. The following detailed description, therefore, is not to be taken in a limiting sense, and the scope of the present disclosure is defined by the appended claims.

Embodiments described herein provide an electronic health record (EHR) storage processing environment that enables secure, seamless sharing of EHRs among healthcare participants (e.g., patients, healthcare providers, payers, and researchers). The environment includes an encrypted data store that stores encrypted EHRs of patients and a metadata tree for each patient that provides a mapping to the EHRs of a given patient in the encrypted data store. Each EHR is uniquely encrypted using a patient key, a provider key, and a location corresponding to the EHR in the metadata tree prior to being stored in the encrypted data store. The metadata tree for each patient is visible to healthcare participants, such as healthcare providers, to allow the participants to store and access EHRs of patients.

To allow EHRs to be stored in the encrypted data store, each healthcare provider uses a unique provider key for each patient (referred to herein as $K_{patient,\ provider}$) that is generated based on a corresponding patient key (referred to herein as $K_{patient}$) of a patient and a provider identifier (referred to herein as provider-id). To store an EHR of a patient, a provider accesses the metadata tree for the patient and determines a location for the EHR in the metadata tree. The provider then generates a record key (referred to herein as $K_{record}$) based on the provider key and the location in the metadata tree, encrypts the EHR using the record key, stores the encrypted EHR in the encrypted data store, and updates the metadata tree to include a reference to the EHR at the determined location. The provider may also generate and share a record key with another healthcare participant to allow the participant to store EHRs on behalf of the provider.

To access an EHR of a patient, a provider accesses the metadata tree for the patient and determines the location that corresponds to the EHR in the metadata tree. If the provider generated the EHR (e.g., if the EHR is one of the provider's records), then the provider accesses the EHR from the encrypted data store, generates the record key based on the provider key and the location of the reference to the EHR in the metadata tree, and decrypts the EHR using the record key. If the provider did not generate the EHR (e.g., if the EHR was generated by another provider), then the provider requests and receives the record key from the other provider or the patient, accesses the EHR from the encrypted data store, and decrypts the EHR using the record key.

Because provider and record keys are generated based on patient keys, patients have the ability to access all records from all providers using the metadata tree. Patients, as well as providers that generate EHRs, may share EHRs with other providers by generating the record keys for selected EHRs and providing the record keys to the other providers. The other providers may select EHRs in which to request access using the metadata tree for the patient. Accordingly, the processing environment described herein enables providers from different healthcare institutions to directly store EHRs of a patient in a common data store and provide access to selected EHRs to other providers.

As used herein, the term "healthcare participant" (also referred to as "participant") refers to a patient, a healthcare provider, a payer, a researcher, or other suitable person involved in a healthcare process of a patient that generates and/or uses healthcare information corresponding to a patient. The term "patient" refers to a person that receives at least one healthcare service from a healthcare provider. The term "healthcare provider" (also referred to as "provider") refers to a person and/or institution that provides at least one healthcare service to a patient.

The term "electronic health record" (EHR) refers to a set of healthcare information generated by a healthcare participant and stored in an electronic format on at least one machine-readable storage medium. The term "encrypted electronic health record" refers to an electronic health record that has been encrypted with an encryption key such as a record key.

The term "patient key" refers to an encryption key of a patient. The term "provider key" refers to an encryption key that is generated based on a patient key and a provider identifier. The term "record key" refers to an encryption key that is generated based on a provider key and a location in a metadata tree of a patient that corresponds to an EHR of the patient. The term "shared key" refers to a record key that is provided from a patient to a provider that did not generate a given EHR or from a provider that generated a given EHR to another, unaffiliated provider.

The term "metadata" refers to a set of information that describes at least one record, such as an electronic health record. The term "metadata tree" refers to a set of nodes that include metadata where each node has a specified relationship with at least one other node in the set.

FIG. 1 is a block diagram illustrating one embodiment of an electronic health record store processing environment 10. Environment 10 includes a patient system 20, a set of provider systems 30(1)-30(M) where M is an integer that is greater than or equal to two, an electronic health record (EHR) manager 40, an electronic health record (EHR) store 50, and a communications network 60. Patient system 20, provider systems 30, EHR manager 40, and EHR store 50 communicate with one another using communications network 60. Environment 10 may be implemented using any suitable type, number, and configuration of processing systems to form patient system 20, provider systems 30, EHR manager 40, and EHR store 50 as well as any suitable type, number, and configuration of communications devices to form communications network 60.

Environment 10 provides the ability to create and manage EHRs of patients including a patient 12 that corresponds to patient system 20 (other patients and patient systems not shown). In one embodiment, patient 12 interacts with patient system 20 to register with EHR manager 40 using a patient manager 42. Patient manager 42 causes patient information of patient 12 to be received and stored in a patient database 44 and initializes a metadata tree 70 (shown in FIG. 2) corresponding to patient 12 in metadata store 56. Patient manager 42 may include portions of the registration information in metadata tree 70 of patient 12 in some embodiments. In other embodiments, patient 12 may register in other suitable ways and/or metadata tree 70 for patient 12 may be initialized in other suitable ways.

Figure 2:
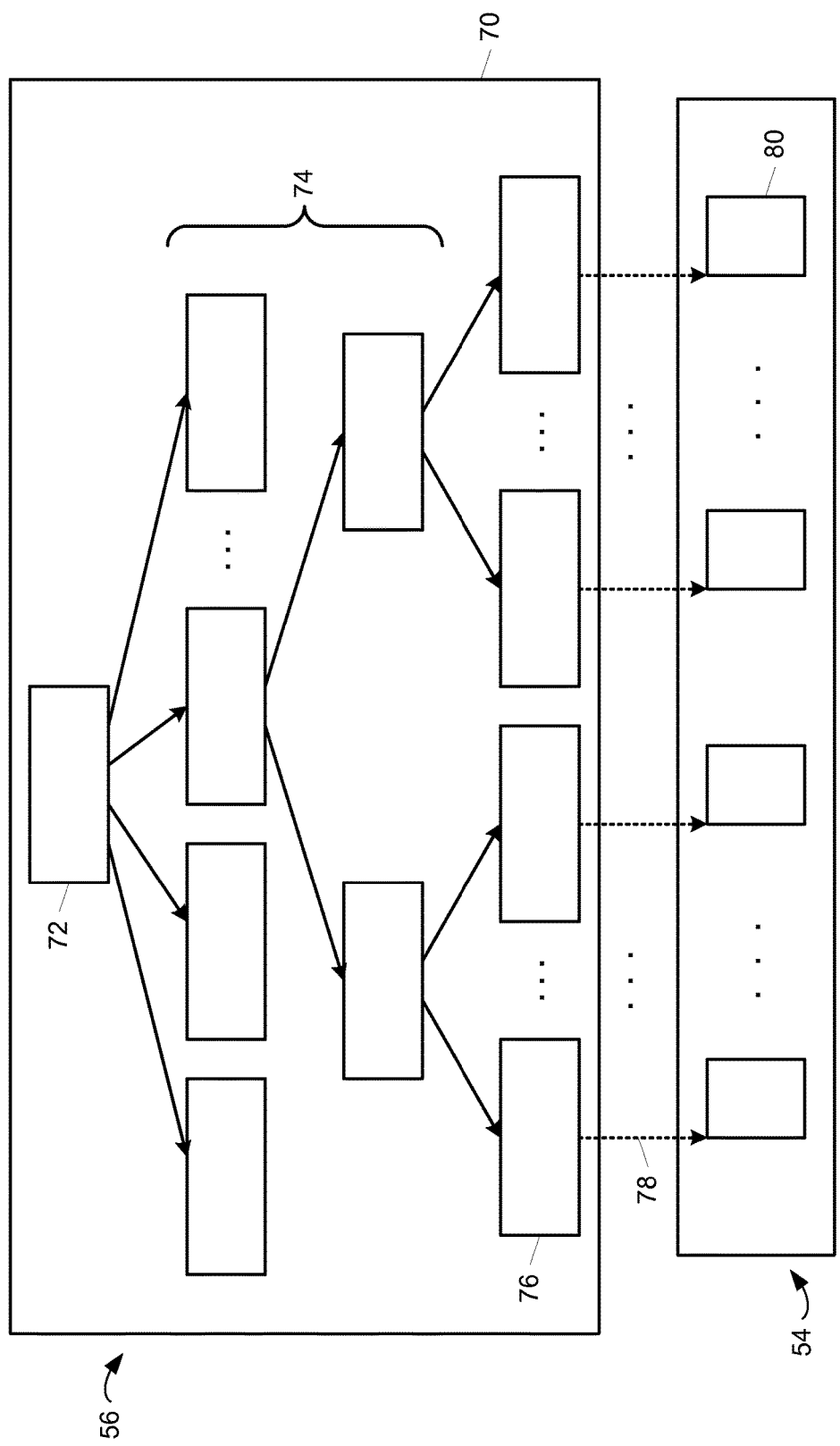
FIG. 2 is a block diagram illustrating one embodiment of a metadata tree and an encrypted data store.

Patient 12 communicates with EHR store 50 using a data access adaptor 24 in patient system 20 to access, store, manage, and share encrypted EHRs 80 of patient 12 (shown in FIG. 2). Data access adaptor 24 communicates with a data access front 52 on EHR store 50 using communications network 60 to access an encrypted data store 54, a metadata store 56, and an audit log 58 in EHR store 50 as described in additional detail below. Patient system 20 stores a patient key 22 ($K_{patient}$) that represents an encryption key that is unique to patient 12. Patient 12 may generate or receive patient key 22 using patient system 20. Patient key 22 may also be stored on a smart card or other suitable processing system (not shown) that includes at least one machine-readable storage media. Patient key 22 provides root access to metadata tree 70 of patient 12.

Providers (not shown) interact with corresponding provider systems 30 to register with EHR manager 40 and receive a corresponding provider identifier 31. A provider manager 46 causes provider information of providers to be received and stored in a provider database 48. Provider manager 46 assigns a provider identifier (provider-id) to each provider and stores the provider-ids in provider database 48. Each provider-id represents information that may be used in combination with a patient key to generate a provider key ($K_{patient, provider}$) for each patient of the provider. Provider manager 46 may provide provider-ids 31 to provider systems 30 in any suitable way such as by transmitting provider-ids 31 to provider systems 30 using communications network 60.

Provider keys for each patient may be generated by patients (e.g., patient 12). To generate a provider key 32, patient system 20 or another suitable processing system (not shown) generates a unique provider key 32 for patient 12 based on patient key 22 and a corresponding provider-id 31. For example, patient system 20 generates a provider key 32(1) based on patient key 22 and provider-id 31(1) and provides provider key 32(1) to provider system 30(1) in any suitable secure way such as via a smart card or via communications network 60. In one embodiment, patient system 20 generates provider keys 32 for each provider using a cryptographic keyed, one-way hash function that generates provider keys 32 as a function of patient key 22 and corresponding provider-ids 31. In other embodiments, other suitable functions may be used to generate provider keys 32 based on patient keys 22 and provider-ids 31. As may be seen, each provider maintains a single provider key 32 for each patient (e.g., each provider system 30 stores a provider key 32 for patient 12).

Provider keys 32 allow a provider to generate encrypted EHRs 80 for patient 12 and store encrypted EHRs 80 in encrypted data store 54. Providers access EHR store 50 using a corresponding data access adaptor 34 to access, store, manage, and share encrypted EHRs 80 of patient 12. Data access adaptor 34 communicates with data access front 52 on EHR store 50 using communications network 60 to access encrypted data store 54, metadata store 56, and audit log 58 in EHR store 50 as described in additional detail below.

In EHR store 50, encrypted data store 54 stores encrypted EHRs 80 of patient 12 as well as encrypted EHRs of other patients (not shown). Encrypted data store 54 includes any suitable type, number, and/or configuration of machine-readable storage media to store the encrypted EHRs. Because the EHRs are encrypted and because encrypted data store 54 does not include encryption keys (i.e., record keys) for the EHRs, encrypted data store 54 does not need to be a trusted data store (e.g., encrypted data store 54 may be owned or operated by one or more untrusted third parties).

Metadata store 56 includes metadata tree 70 for patient 12 as well as metadata trees of other patients (not shown). As shown in FIG. 2, metadata tree 70 represents a hierarchical tree structure with a root node 72, any number of intermediate nodes 74, and a single leaf node 76 for each encrypted EHR 80 where each leaf node 76 stores metadata regarding a corresponding encrypted EHR 80. Root node 72 may include information that identifies patient 12, intermediate nodes 74 represent logical groupings of EHRs (e.g., by provider or by categories of patient information such as treatment conditions) and include information that describes the groupings, and leaf nodes 76 each include a single, unique reference 78 to a corresponding encrypted EHR 80 in encrypted data store 54 as well as information that describes the corresponding encrypted EHRs 80. References 78 may be used to access encrypted EHRs 80 in encrypted data store 54. In one embodiment, the entire metadata tree 70 is accessible by patient 12 and all providers that have registered with EHR manager 40. In other embodiments, other security measures, such as encryption, may be applied to metadata tree 70 to limit access to metadata tree 70 to desired healthcare participants.

Metadata tree 70 allows unaffiliated providers (e.g., providers practicing under different, unrelated business entities) to store different encrypted EHRs 80 of patient 12 to encrypted data store 54. Encrypted EHRs 80 are each encrypted with different record keys such that a record key for one encrypted EHR 80 may not be used to decrypt any other encrypted EHR 80. Providers may use metadata tree 70 to determine which encrypted EHRs 80 they need to access and can request access (i.e., record keys) from other providers that generated the needed encrypted EHRs 80 or patient 12 as described in additional detail below.

EHR store 50 maintains audit log 58 to log all data accesses to encrypted data store 54 and metadata store 56. Audit log 58 may be used for audit or other suitable purposes.

Communications network 60 includes any suitable type, number, and combination of wired and/or wireless communications devices that allow patient system 20, provider systems 30, EHR manager 40, and EHR store 50 to communicate with one another.

Figure 6:
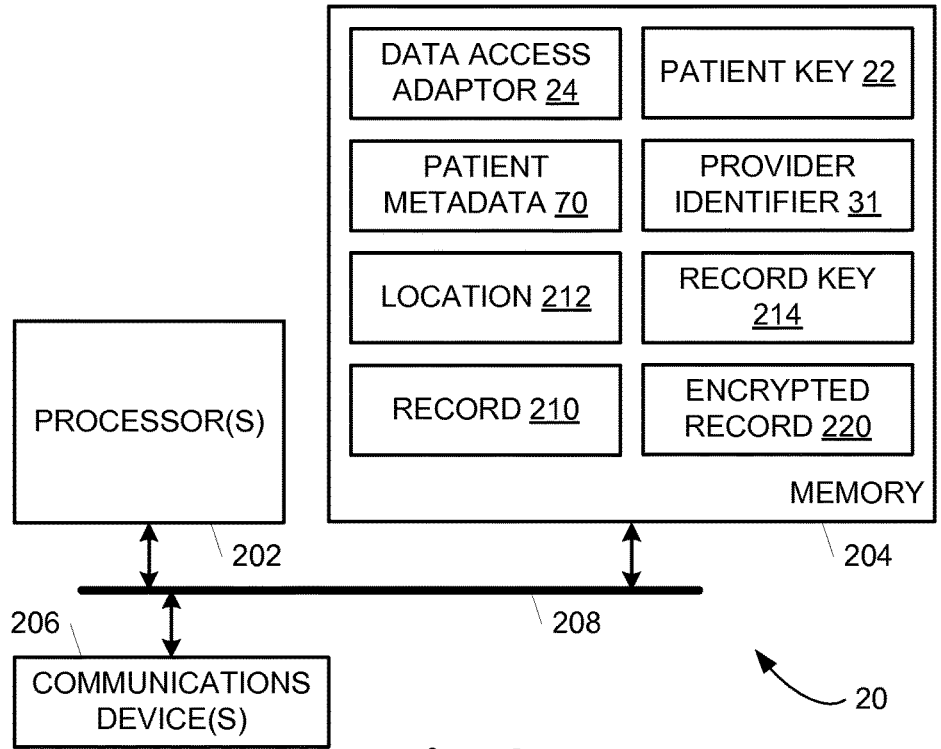
FIG. 6 is a block diagram illustrating one embodiment of a patient system.

Environment 10 including, patient system 20, provider systems 30, EHR manager 40, and EHR store 50 may be implemented with any suitable type, number, and configuration of processing systems that each include one or more processors for executing instructions stored in one or more memories. In addition, data access front 52, encrypted data store 54, metadata store 56, and audit log 58 may be implemented using different processing systems in some embodiments. Embodiments of patient system 20 and provider systems 30 are shown in FIGS. 6 and 3, respectively, and described in additional detail below.

Figure 3:
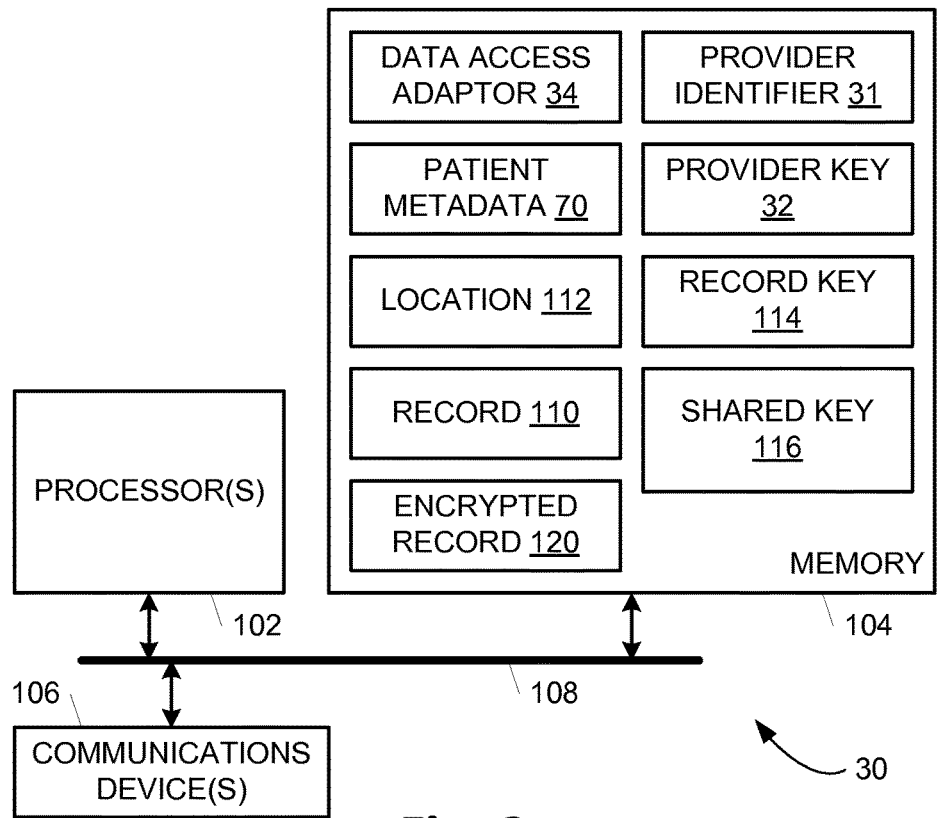
FIG. 3 is a block diagram illustrating one embodiment of a provider system.

FIG. 3 is a block diagram illustrating one embodiment of a provider system 30. Provider system 30 includes a set of one or more processors 102 configured to execute a set of instructions stored in a memory system 104, memory system 104, and at least one communications device 106. Processors 102, memory system 104, and communications devices 106 communicate using a set of interconnections 108 that includes any suitable type, number, and/or configuration of controllers, buses, interfaces, and/or other wired or wireless connections.

Provider system 30 represents any suitable processing device or portion of a processing device such as a server computer, a laptop computer, a tablet computer, a desktop computer, a mobile telephone with processing capabilities (i.e., a smart phone), or another suitable type of electronic device with processing capabilities. Each processor 102 is configured to access and execute instructions stored in memory system 104 and to access and store data in memory system 104. Memory system 104 includes any suitable type, number, and configuration of volatile or non-volatile machine-readable storage media configured to store instructions and data. Examples of machine-readable storage media in memory system 104 include hard disk drives, random access memory (RAM), read only memory (ROM), flash memory drives and cards, and other suitable types of magnetic and/or optical disks. The machine-readable storage media are considered to be part of an article or article of manufacture. An article or article of manufacture refers to one or more manufactured components. Communications devices 106 include any suitable type, number, and/or configuration of communications devices configured to allow provider system 30 to communicate across one or more wired or wireless networks such as communications network 60 (shown in FIG. 1).

Figure 4:
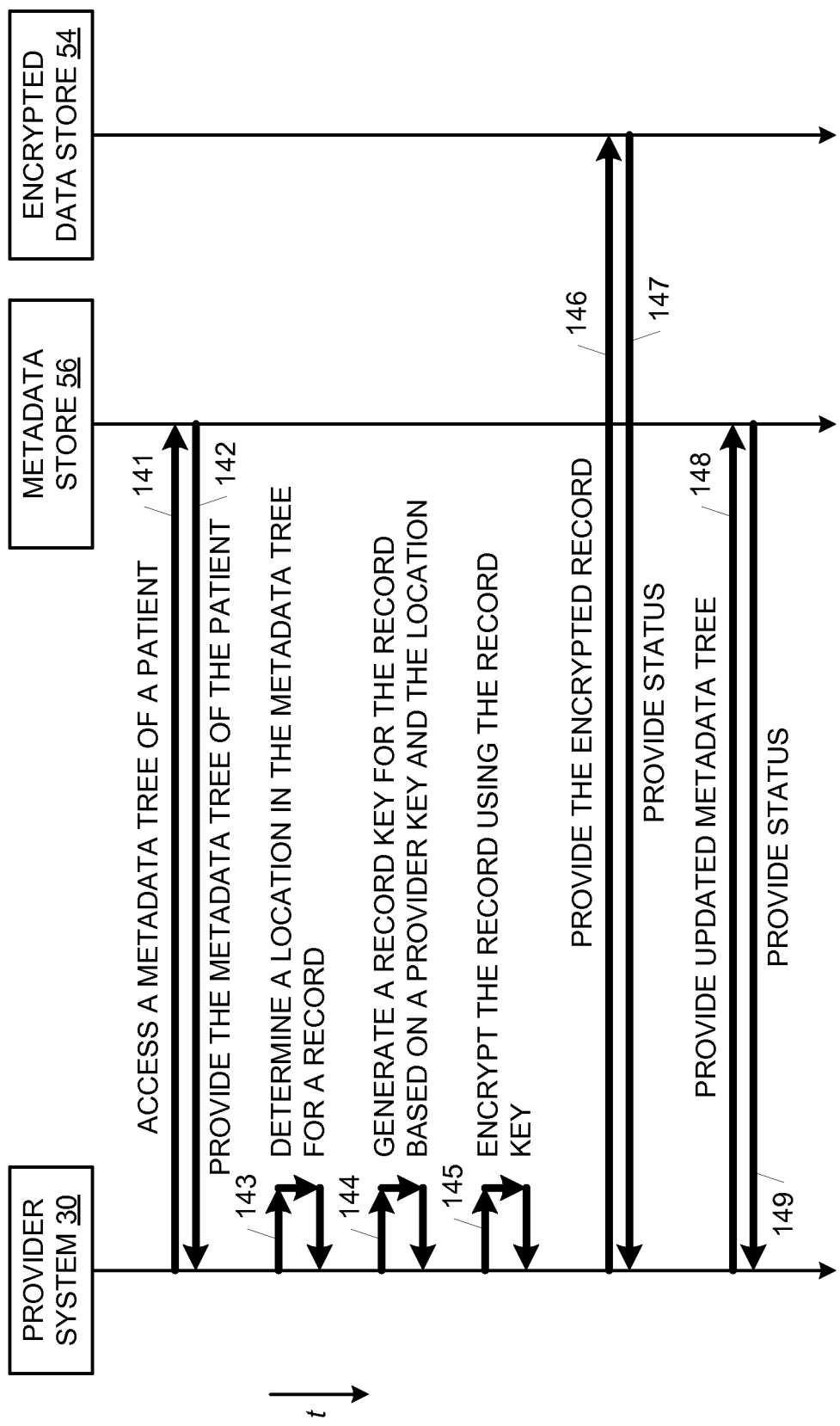
FIG. 4 is a schematic diagram illustrating one embodiment of storing an encrypted record using a provider key.
Figure 5:
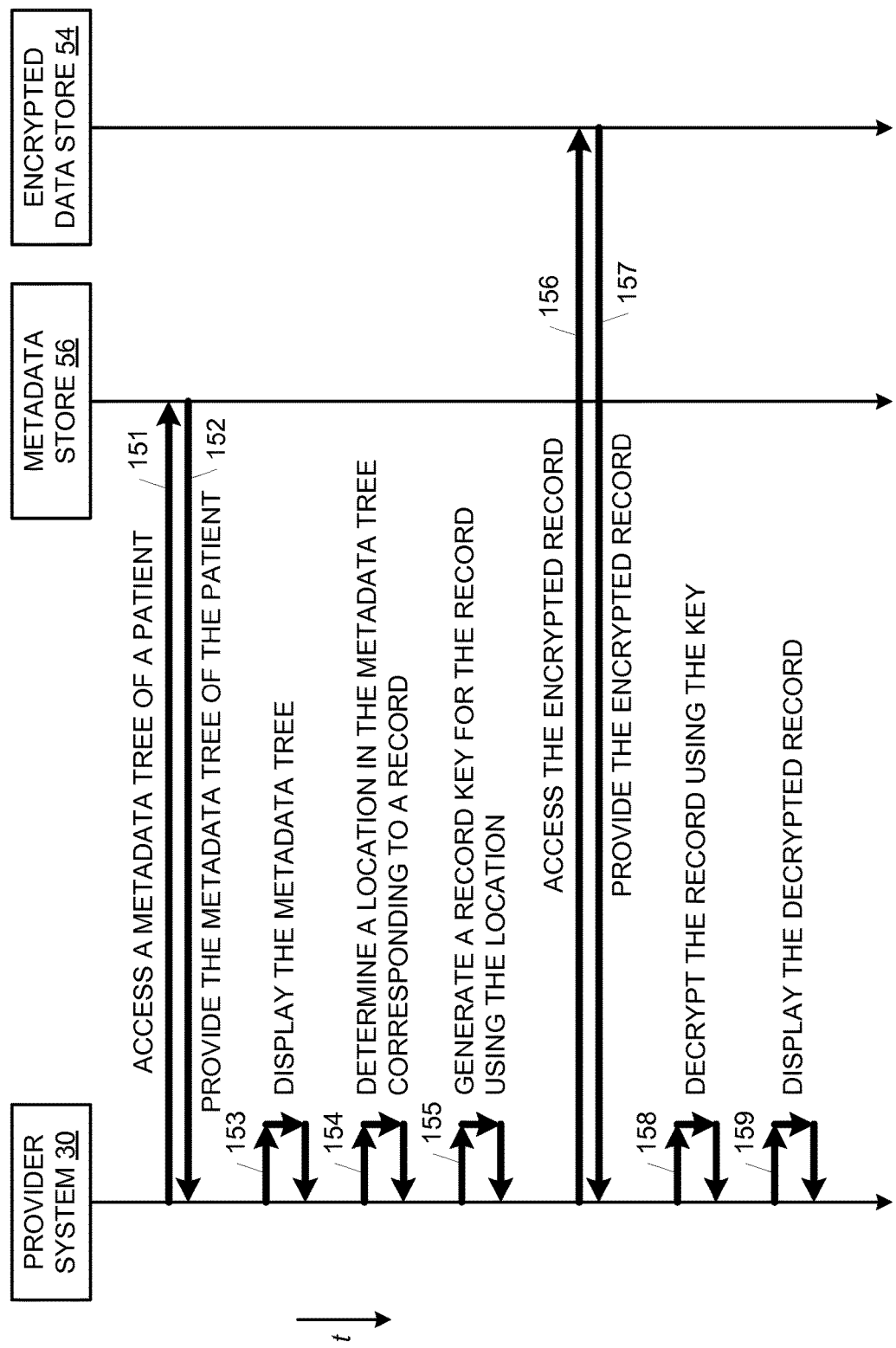
FIG. 5 is a schematic diagram illustrating one embodiment of accessing an encrypted record using a provider key.

Data access adaptor 34 includes instructions that, when executed by processors 102, causes processors 102 to perform the functions of data access adaptor 34 that will now be described with reference to FIGS. 4 and 5. FIG. 4 is a schematic diagram illustrating one embodiment of storing an encrypted record 80 using a provider key 32, and FIG. 5 is a schematic diagram illustrating one embodiment of accessing an encrypted record using a provider key.

Referring to FIGS. 3 and 4, data access adaptor 34 accesses metadata tree 70 of patient 12 from metadata store 56 through data access front 52 as indicated by an arrow 141. Metadata store 56 provides metadata tree 70 to provider system 30 through data access front 52 as indicated by an arrow 142. Data access adaptor 34 determines a location 112 in metadata tree 70 for a new or updated EHR 110 as indicated by an arrow 143. Location 112 represents a fully qualified path in metadata tree 70 (i.e., a uniform resource identifier (URI)). Data access adaptor 34 generates a record key 114 ($K_{record}$) based on provider key 32 ($K_{patient, provider}$) and location 112 as indicated by an arrow 144. Data access adaptor 34 encrypts EHR 110 using record key 114 to generate an encrypted EHR 120 as indicated by an arrow 145.

Data access adaptor 34 provides encrypted EHR 120 to encrypted data store 54 through data access front 52 as indicated by an arrow 146. Encrypted data store 54 provides a status to data access adaptor 34 through data access front 52 as indicated by an arrow 147. If the status indicates that encrypted EHR 120 was not stored successfully, then data access adaptor 34 may retry the store. Once the store is successful, data access adaptor 34 updates metadata tree 70 to add a leaf node 76 to include a reference 78 to the successfully stored encrypted EHR 80 in encrypted data store 54 and provides the updated metadata tree 70 to metadata store 56 through data access front 52 as indicated by an arrow 148. Metadata store 56 provides a status to data access adaptor 34 through data access front 52 as indicated by an arrow 149. If the status indicates that the updated metadata tree 70 was not stored successfully, then data access adaptor 34 may retry the update.

Data access adaptor 34 repeats the process shown in FIG. 4 for each EHR that is stored in encrypted data store 54.

Once a provider stores an encrypted EHR 80 to encrypted data store 54, the provider may access the encrypted EHR 80 from encrypted data store 54 as shown in FIG. 5.

Referring to FIGS. 3 and 5, data access adaptor 34 accesses metadata tree 70 of patient 12 from metadata store 56 through data access front 52 as indicated by an arrow 151. Metadata store 56 provides metadata tree 70 to provider system 30 through data access front 52 as indicated by an arrow 152. Data access adaptor 34 displays metadata tree 70 to the provider to allow the provider to select a desired encrypted EHR 80 as indicated by an arrow 153. Data access adaptor 34 determines a location 112 in metadata tree 70 corresponding to the encrypted EHR 80 as indicated by an arrow 154. As noted above, location 112 represents a fully qualified path in metadata tree 70 (i.e., a uniform resource identifier (URI)). Data access adaptor 34 generates a record key 114 ($K_{record}$) based on provider key 32 ($K_{patient, provider}$) and location 112 as indicated by an arrow 155.

Data access adaptor 34 accesses the encrypted EHR 80 from encrypted data store 54 through data access front 52 as indicated by an arrow 156. Encrypted data store 54 provides the desired encrypted EHR 80 through data access front 52 as indicated by an arrow 157. Data access adaptor 34 stores the encrypted EHR 80 (shown as encrypted EHR 120) and decrypts encrypted EHR 120 into a decrypted EHR 110 using record key 114 as indicated by an arrow 158. Data access adaptor 34 displays decrypted EHR 110 to the provider as indicated by an arrow 159.

Data access adaptor 34 repeats the process shown in FIG. 5 for each encrypted EHR generated by a provider that is accessed from encrypted data store 54 by the provider.

FIG. 6 is a block diagram illustrating one embodiment of patient system 20. Patient system 20 includes a set of one or more processors 202 configured to execute a set of instructions stored in a memory system 204, memory system 204, and at least one communications device 206. Processors 202, memory system 204, and communications devices 206 communicate using a set of interconnections 208 that includes any suitable type, number, and/or configuration of controllers, buses, interfaces, and/or other wired or wireless connections.

Patient system 20 represents any suitable processing device or portion of a processing device such as a server computer, a laptop computer, a tablet computer, a desktop computer, a mobile telephone with processing capabilities (i.e., a smart phone), or another suitable type of electronic device with processing capabilities. Each processor 202 is configured to access and execute instructions stored in memory system 204 and to access and store data in memory system 204. Memory system 204 includes any suitable type, number, and configuration of volatile or non-volatile machine-readable storage media configured to store instructions and data. Examples of machine-readable storage media in memory system 104 include hard disk drives, random access memory (RAM), read only memory (ROM), flash memory drives and cards, and other suitable types of magnetic and/or optical disks. The machine-readable storage media are considered to be part of an article or article of manufacture. An article or article of manufacture refers to one or more manufactured components. Communications devices 206 include any suitable type, number, and/or configuration of communications devices configured to allow patient system 20 to communicate across one or more wired or wireless networks such as communications network 60 (shown in FIG. 1).

Figure 7:
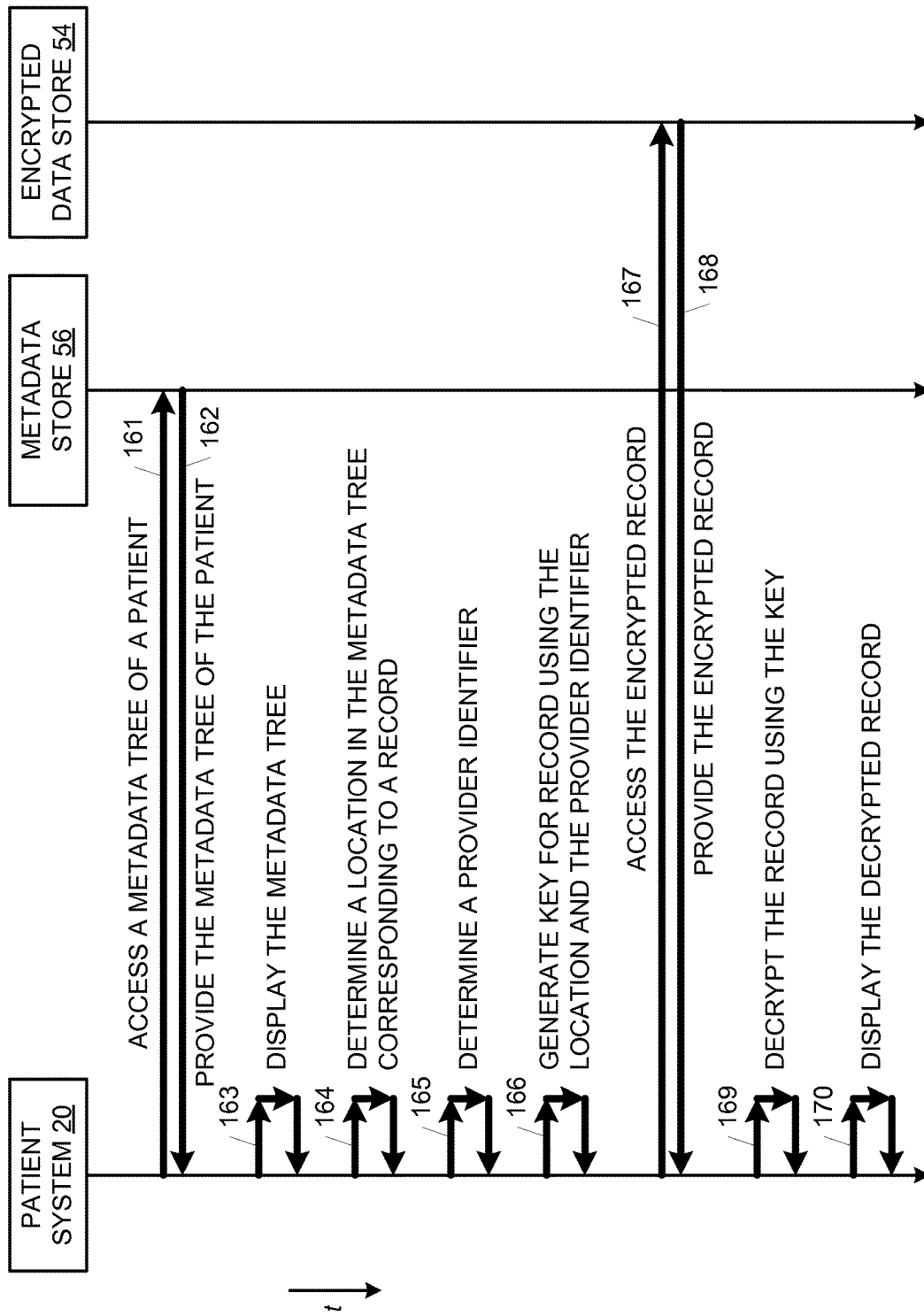
FIG. 7 is a schematic diagram illustrating one embodiment of accessing an encrypted record using a patient key.

Data access adaptor 24 includes instructions that, when executed by processors 202, causes processors 202 to perform the functions of data access adaptor 24 that will now be described with reference to FIG. 7. FIG. 7 is a schematic diagram illustrating one embodiment of accessing an encrypted record 80 using a patient key 22. The process of FIG. 7 allows patient 12 to may access any encrypted EHR 80 from encrypted data store 54 (i.e., encrypted EHRs 80 generated by any provider). In particular, patient 12 may generate any record key 214 using patient key 22, the provider-id 31 of the provider that generated the encrypted EHR 80, and a location 212 in metadata tree 70 corresponding to the encrypted EHR 80.

Referring to FIGS. 6 and 7, data access adaptor 24 accesses metadata tree 70 of patient 12 from metadata store 56 through data access front 52 as indicated by an arrow 161. Metadata store 56 provides metadata tree 70 to patient system 20 through data access front 52 as indicated by an arrow 162. Data access adaptor 24 displays metadata tree 70 to patient 12 to allow patient 12 to select a desired encrypted EHR 80 as indicated by an arrow 163. Data access adaptor 24 determines a location 212 in metadata tree 70 corresponding to the encrypted EHR 80 as indicated by an arrow 164. As noted above, location 212 represents a fully qualified path in metadata tree 70 (i.e., a uniform resource identifier (URI)). Data access adaptor 24 determines a provider-id 31 of the provider that generated the encrypted EHR 80 (e.g., by accessing provider-id 31 from EHR manager 40) as indicated by an arrow 165. Data access adaptor 24 generates a record key 214 ($K_{record}$) based on patient key 22 ($K_{patient}$), provider-id 31, and location 212 as indicated by an arrow 166.

Data access adaptor 24 accesses the encrypted EHR 80 from encrypted data store 54 through data access front 52 as indicated by an arrow 167. Encrypted data store 54 provides the encrypted EHR 80 through data access front 52 as indicated by an arrow 168. Data access adaptor 24 stores the encrypted EHR 80 (shown as encrypted EHR 220 in FIG. 3) and decrypts encrypted EHR 220 into a decrypted EHR 210 as indicated by an arrow 169. Data access adaptor 24 displays decrypted EHR 210 to patient 12 as indicated by an arrow 170.

Data access adaptor 24 repeats the process shown in FIG. 7 for each encrypted EHR that is accessed from encrypted data store 54 by patient 12.

As described above, both providers that generate encrypted EHRs 80 and patient 12 may generate record keys 114 and 214, respectively, which are used to decrypt the encrypted EHRs 80. To share an encrypted EHR 80 with another provider, either the provider that generates the encrypted EHR 80 or patient 12 shares record key 114 or 214, respectively, to allow the other provider to access and decrypt the encrypted EHR 80.

Figure 8:
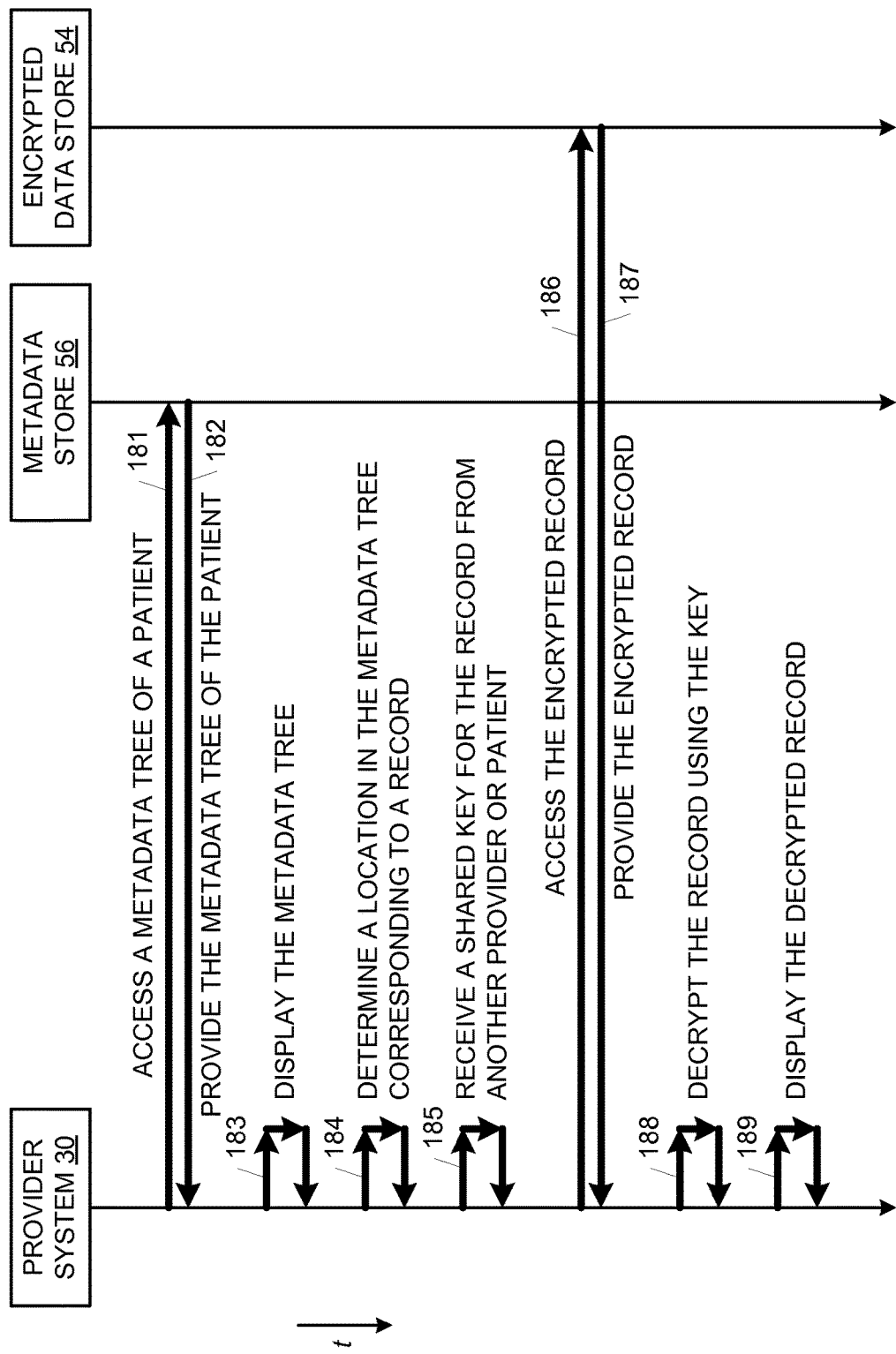
FIG. 8 is a schematic diagram illustrating one embodiment of accessing an encrypted record using a shared key.

Referring back to FIG. 3, data access adaptor 34 further includes instructions that, when executed by processors 102, causes processors 102 to perform the functions of data access adaptor 34 that will now be described with reference to FIG. 8. FIG. 8 is a schematic diagram illustrating one embodiment of accessing an encrypted record using a shared key.

Referring to FIGS. 3 and 8, data access adaptor 34 accesses metadata tree 70 of patient 12 from metadata store 56 through data access front 52 as indicated by an arrow 181. Metadata store 56 provides metadata tree 70 to provider system 30 through data access front 52 as indicated by an arrow 182. Data access adaptor 34 displays metadata tree 70 to the provider to allow the provider to select a desired encrypted EHR 80 as indicated by an arrow 183. Data access adaptor 34 determines a location 112 in metadata tree 70 corresponding to the encrypted EHR 80 as indicated by an arrow 184. As noted above, location 112 represents a fully qualified path in metadata tree 70 (i.e., a uniform resource identifier (URI)). Data access adaptor 34 receives a shared key 116 for the encrypted EHR 80 from another provider or patient 12 as indicated by an arrow 185.

Data access adaptor 34 accesses the encrypted EHR 80 from encrypted data store 54 through data access front 52 as indicated by an arrow 186. Encrypted data store 54 provides the desired encrypted EHR 80 through data access front 52 as indicated by an arrow 187. Data access adaptor 34 stores the encrypted EHR 80 (shown as encrypted EHR 120) and decrypts encrypted EHR 120 into a decrypted EHR 110 using shared key 116 as indicated by an arrow 188. Data access adaptor 34 displays decrypted EHR 110 to the provider as indicated by an arrow 189.

Data access adaptor 34 repeats the process shown in FIG. 8 for each encrypted EHR generated by one provider that is accessed from encrypted data store 54 by another provider.

Providers may also store encrypted EHRs 120 on behalf of other providers by using shared key 116 in a variation of the embodiment of FIG. 4. To do so, a provider uses data access adaptor 34 to receive shared key 116 for the encrypted EHR 80 from another provider and omits step 144 in FIG. 4. Data access adaptor 34 encrypts an EHR 110 using shared key 116, rather than record key 114, to generate an encrypted EHR 120 in step 145 and performs the remaining steps of FIG. 4 as described above.

The above embodiments may advantageously allow patients to securely manage access to EHRs created by different healthcare providers in a common encrypted data store. The embodiments allow a patient to maintain a single encryption key and allow providers to maintain a single encryption key per patient. The patient may access all EHRs using the patient key, and providers may access all EHRs using either a provider key or a shared key from another provider or the patient. In addition, the metadata tree provides the patient and providers with the ability to navigate a patient's entire health history while preserving privacy and security. As a result, the embodiments may shift the primary responsibility of making record access decisions to the providers while ensuring that the patient has access to all EHRs at any time.

What is claimed is:

1. A method performed by a processing system, the method comprising:
   receiving a patient key from a patient;
   accessing a provider identifier corresponding to a first provider;
   generating a first provider key based on the patient key and the provider identifier;
   determining a first location in a metadata tree of the patient for a first electronic health record;
   generating a first record key for the first electronic health record based on the first location and the first provider key corresponding to the first provider;
   encrypting the first electronic health record using the first record key to generate a first encrypted record;
   providing the first encrypted record to an encrypted data store;
   updating the first location in the metadata tree to include a first reference to the first encrypted record in the encrypted data store; and
   providing the metadata tree to a metadata store that is accessible by a second provider.

2. The method of claim 1 wherein a second location in the metadata tree includes a second reference to a second encrypted record in the encrypted data store, wherein the second encrypted electronic health record is generated by a second provider, and wherein the second provider is not affiliated with the first provider.

3. The method of claim 2 further comprising:
   receiving a second record key for the second encrypted record, the second record key generated based on the second location in the metadata tree that includes the second reference and a second provider key corresponding to the second provider, the second provider key generated from the patient key;
   accessing the second encrypted record from the encrypted data store; and
   decrypting the second encrypted record using the second record key.

4. The method of claim 1 further comprising:
   determining a second location in the metadata tree of the patient for a second electronic health record;
   generating a second record key for the second electronic health record based on the second location and the first provider key;
   encrypting the second electronic health record using the second record key to generate a second encrypted record; and
   providing the second encrypted record to the encrypted data store.

5. The method of claim 4 wherein the first record key differs from the second record key such that the first record key is not usable to decrypt the second encrypted record and the second record key is not usable to decrypt the first encrypted record.

6. A processing system comprising:
   a set of one or more processors; and
   a memory storing a set of instructions that, when executed by the set of processors, cause the set of processors to:
      access a metadata tree from a metadata store that is accessible to a patient, a first provider, and a second provider that is not affiliated with the first provider;
      determine a first location in the metadata tree of the patient that corresponds to a first encrypted electronic health record in an encrypted data store;
      generate a first record key for the encrypted electronic health record based on the first location and a first provider key corresponding to first provider;
      generate the first provider key based on a patient key corresponding to the patient;
      access the first encrypted electronic health record from the encrypted data store using the first reference; and
      decrypt the first encrypted electronic health record using the first record key.

7. The processing system of claim 6 wherein the first location in the metadata tree includes a first reference to the first encrypted electronic health record in the encrypted data store, wherein a second location in the metadata tree includes a second reference to a second encrypted electronic health record in the encrypted data store, wherein the second encrypted electronic health record is generated by the second provider, and wherein the second provider is not affiliated with the first provider.

8. The processing system of claim 7 wherein the first record key is not usable to decrypt the second encrypted electronic health record, wherein a second record key is usable to decrypt the second encrypted electronic health record, and wherein the second record key is not usable to decrypt the first encrypted electronic health record.

9. An article comprising at least one non-transitory machine-readable storage medium storing instructions that, when executed by a processing system, cause the processing system to:
   access a metadata tree comprising a first location including a first reference to a first encrypted electronic health record in an encrypted data store and a second location including a second reference to a second encrypted electronic health record in the encrypted data store, wherein the second encrypted electronic health record is generated by a second provider that is not affiliated with a first provider;
   determine the first location in the metadata tree of a patient that corresponds to the first encrypted electronic health record, the first encrypted electronic health record generated by the first provider;
   receive a first record key for the first encrypted electronic health record, the first record key generated based on the first location and a first provider key corresponding to the first provider, the first provider key generated based on a patient key corresponding to the patient;
   update the first location in the metadata tree to include the first reference to the first encrypted electronic health record in the encrypted data store;
   access the first encrypted electronic health record from the encrypted data store using the first reference; and
   decrypt, by the second provider, the first encrypted electronic health record using the first record key.

10. The article of claim 9, wherein the first record key is not usable to decrypt the second encrypted electronic health record, wherein a second record key is usable to decrypt the second encrypted electronic health record, and wherein the second record key is not usable to decrypt the first encrypted electronic health record.

11. The article of claim 9, wherein the instructions, when executed by the processing system, cause the processing system to:
   request the first record key from the first provider; and
   receive the first record key from the first provider.

12. The article of claim 9, wherein the instructions, when executed by the processing system, cause the processing system to:
   request the first record key from the patient; and
   receive the first record key from the patient.

13. The article of claim 9, wherein the instructions, when executed by the processing system, cause the processing system to:
   determine the second location in the metadata tree of the patient for the second encrypted electronic health record;
   receive a second record key for the second encrypted electronic health record based on the second location and the first provider key;
   update the second location in the metadata tree to include the second reference to the second encrypted electronic health record in the encrypted data store;
   access the second encrypted electronic health record from the encrypted data store using the second reference; and
   decrypt, by the second provider, the second encrypted electronic health record using the second record key.

14. The article of claim 13, wherein the instructions, when executed by the processing system, cause the processing system to:
   request the second record key from the first provider; and
   receive the second record key from the first provider.

15. The article of claim 13, wherein the instructions, when executed by the processing system, cause the processing system to:
   request the second record key from the patient; and
   receive the second record key from the patient.

* * * * *